(12) United States Patent
Harpaz et al.

(10) Patent No.: US 11,033,720 B2
(45) Date of Patent: Jun. 15, 2021

(54) CERVICAL CANAL DILATION DEVICE

(71) Applicant: Aqueduct Medical Ltd., Nazareth Illit (IL)

(72) Inventors: Omer Harpaz, Kibbutz Yizrael (IL); Amnon Weichselbaum, Haifa (IL)

(73) Assignee: Aqueduct Medical Ltd., Nazareth Illit (IL)

( * ) Notice: Subject to any disclaimer, the term of this patent is extended or adjusted under 35 U.S.C. 154(b) by 218 days.

(21) Appl. No.: 15/928,116

(22) Filed: Mar. 22, 2018

(65) Prior Publication Data
US 2018/0207409 A1 Jul. 26, 2018

Related U.S. Application Data

(63) Continuation of application No. 15/319,784, filed on Dec. 18, 2016, now Pat. No. 10,512,760.

(51) Int. Cl.
*A61M 25/10* (2013.01)
*A61B 1/00* (2006.01)
(Continued)

(52) U.S. Cl.
CPC ..... *A61M 25/1011* (2013.01); *A61B 1/00082* (2013.01); *A61B 1/00091* (2013.01);
(Continued)

(58) Field of Classification Search
CPC .......... A61M 25/1011; A61M 25/1002; A61M 25/104; A61M 25/10; A61M 2025/1052;
(Continued)

(56) References Cited

U.S. PATENT DOCUMENTS 4,423,725 A * 1/1984 Baran ............... A61M 16/0479
128/207.15
4,976,692 A 12/1990 Atad
(Continued)

FOREIGN PATENT DOCUMENTS

CN 201079622 7/2008
WO 2004052185 11/2004
(Continued)

*Primary Examiner* — Mohamed G Gabr
(74) *Attorney, Agent, or Firm* — Mark M. Friedman

(57) ABSTRACT

There is provided a cervical canal dilator device having a hollow shaft having proximal and distal ends. The shaft is covered on an end portion of the distal end by a slidable protective sleeve. There is at least one inflatable dilating balloon formed on the distal end of the shaft. There is at least one tube extending internally along the shaft and connected to the at least one balloon for inflation thereof, the tube having a connection port on the proximal end of the shaft. A camera is situated at the tip of the distal end of the shaft and a plurality of ejection orifices are formed on the shaft, adjacent to the camera, and anywhere else along it. The shaft is inserted into a patient's cervical canal while viewing the canal via the camera for guidance, and safe and easy placement of the hollow shaft during the insertion, and where the at least one balloon is inflated by introducing a substance via the connection port, the inflated balloon causing dilation of the cervical canal, the shaft being removed from the patient when the cervical canal is dilated.

10 Claims, 8 Drawing Sheets

(51) Int. Cl.
*A61B 1/303* (2006.01)
*A61M 29/02* (2006.01)
*A61M 31/00* (2006.01)

(52) U.S. Cl.
CPC ...... *A61B 1/00135* (2013.01); *A61B 1/00154* (2013.01); *A61B 1/303* (2013.01); *A61M 29/02* (2013.01); *A61M 31/00* (2013.01); *A61M 2025/1015* (2013.01); *A61M 2025/1052* (2013.01); *A61M 2025/1081* (2013.01); *A61M 2210/1433* (2013.01)

(58) Field of Classification Search
CPC .... A61M 2025/1013; A61M 2025/105; A61M 25/1018; A61M 25/10181; A61M 29/02; A61M 16/0481; A61M 16/04; A61M 2210/1433; A61B 17/0218; A61B 17/22; A61B 17/42; A61B 17/12136; A61B 17/4241; A61B 17/7065; A61B 17/12045; A61B 17/12186; A61B 2017/00557; A61B 2017/0256; A61B 2017/22054; A61B 2017/22062; A61B 2017/22055
See application file for complete search history.

(56) References Cited

U.S. PATENT DOCUMENTS

| | | |
|---|---|---|
| 5,722,983 A | 3/1998 | Van Der Weegen |
| 2002/0111602 A1 | 8/2002 | Ackerman et al. |
| 2004/0153116 A1 | 8/2004 | Nobles |
| 2005/0049509 A1 | 3/2005 | Mansour |
| 2005/0267509 A1 | 12/2005 | Davis |
| 2006/0058831 A1 | 3/2006 | Atad |
| 2007/0288051 A1 | 12/2007 | Beyer et al. |
| 2014/0364692 A1* | 12/2014 | Salman .............. A61B 1/00091 600/109 |

FOREIGN PATENT DOCUMENTS

| | | | |
|---|---|---|---|
| WO | 2006128194 | 11/2006 | |
| WO | WO-2016001911 A1 * | 1/2016 | ............ A61M 31/00 |

\* cited by examiner

CERVICAL CANAL DILATION DEVICE

CROSS-REFERENCE TO RELATED APPLICATIONS

The present invention is a Continuation-In-Part of U.S. patent application Ser. No. 15/319,784 which claims the priority date of U.S. Provisional Patent Application No. 62/018,609 filed on Jun. 29, 2014, by the Applicant herein.

FIELD OF THE INVENTION

The present invention relates to catheters. More specifically, the present invention relates to catheters for performing cervical canal dilations using a camera providing vision.

BACKGROUND OF THE INVENTION

The terms "distal" and "proximal" in the context of the present text refer to the direction of the end-portions of the dilation device positioned in the cervical canal in regards to the inner and outer orifices of the cervical canal, respectively.

Approximately 3 million cervical canal dilations are performed annually in the United States for the purpose of intra-uterine procedures. These procedures include: abortions, hysteroscopies and other curettages. Cervical canal dilation allows medical practitioners greater access to the inside of the uterus in order to insert surgical tools for the completion of intra-uterine procedures.

Presently there are primarily two mechanical techniques for dilating the cervix. The first technique is the insertion of hygroscopic rods such as Laminaria (dry, sterile seaweed) or synthetic osmotic dilators into the cervix. When either Laminaria or synthetic osmotic dilators come into contact with body fluids, they expand and this enlarges the opening of the cervix. Often, this process requires two patient-visits and approximately 10-12 hours for sufficient dilation to occur.

The second technique, referred to as rigid rod dilation such as a Hegar rod, involves the insertion and removal of metal or plastic rods that are graduated in increasing diameter. This process is painful, requires the use of anesthesia, and is associated with a risk of uterine and cervix damage and cervical incompetence.

In addition to the two primarily cervix dilating techniques mentioned above, there are techniques in which cervix dilation is achieved by the use of inflated balloons. In U.S. patent application 2007/0288051 Beyer et al. disclose a cervical canal dilator device in which an elongate tubular or cylindrical shaft is inserted into the cervical canal. The shaft is provided with internal cavities that communicate with several dilation-balloons in such a manner as to permit separate inflation of the balloons. A balloon is positioned on the distal end of the shaft and anchors the dilator against the bottom of the cervix when inflated after the dilator is inserted into the cervix and the remaining dilation balloons are positioned between the distal and proximal ends so as to effect optimum dilation of the cervical canal when inflated.

In PCT publication WO2004/052185 Foltz et al. disclose a cervical canal dilating device and method that includes a plastic shaft, and two inflatable members. The shaft can range from being rigid to being highly flexible. One of the inflatable members is fabricated of a non-elastic material and is configured to have a maximum inflatable diameter. The second inflatable member is configured to have a predetermined maximum inflatable diameter. A control system includes means for measuring pressure configured for at least monitoring the pressure of the second inflatable member. When deploying, the dilating device is inserted into the cervical canal. The first inflatable member is expanded in the uterus. The second inflatable member is positioned in the cervical canal and gradually inflated to a predetermined maximum diameter.

The above-mentioned cervix dilating devices are cumbersome to use and do not give the professional operator the ability to readily adjust the procedure to the physiological requirement of any individual treated woman.

The use of inflated balloons for the sealing of the cervical canal is described in the devices disclosed in the U.S.-patent and U.S. patent application given below: In U.S. Pat. No. 4,976,692 to Atad, there is disclosed a device in which two distantly positioned balloons are connected to a catheter that is inserted into the cervical canal. When the catheter is inserted the balloons are inflated so as to cover and seal the internal and external opening of the cervical canal. An opening located between the balloons enables confined input of medical gel or solution through the catheter into the cervical canal. Atad's device relates to widening of the cervical canal prior to giving birth and does not relate to and is not able to perform controlled cervical canal dilation procedures in treated patients.

In U.S. patent application 2002/0111602 to Ackerman et al., there is disclosed a non-surgical catheter device for entry into a uterus. The device includes an elongated balloon that is inserted into the cervical canal of the uterus and a tube that extends through the balloon from the external opening of the cervix to the internal opening of the cervix and into the uterus. By inflating the balloon, the two sections extending from the cervical canal increase in size and seal the passage through the canal. Through an opening adjacent to or at the end of the tube, diagnostic fluid is dispensed into the uterus. Ackerman's device relates to uterus medical treatment procedures and does not relate to and is not able to perform controlled cervical canal dilation procedures in treated patients.

The cervical canal dilator of the present invention provides a user-friendly solution that overcomes the above mentioned disadvantages of the current dilators and enables controlled radial dilation of the cervix (to a predetermined diameter) within a few minutes.

SUMMARY OF THE INVENTION

The cervical canal dilation device of the present invention relates to controlled injection of liquid or gel for inflating balloons located in the cervical canal in order to obtain a desired predetermined dilation while causing the treated woman minimal discomfort.

In accordance with a preferred embodiment of the present invention there is provided a cervical canal dilator device comprising:

a hollow shaft having proximal and distal ends, said shaft covered on an end portion of said distal end by a slidable protective sleeve;

at least one inflatable dilating balloon formed on said distal end of said shaft;

at least one tube extending internally along said shaft and connected to said at least one balloon for inflation thereof, said tube having a connection port on said proximal end of said shaft;

at least one ejection orifice formed on said shaft; and a camera situated at the tip of said distal end of said shaft, wherein said shaft is inserted into a patient's cervical canal while viewing the canal via said camera for guidance, and safe and easy placement of said hollow shaft during said insertion, and wherein said at least one balloon is inflated by introducing a substance via said connection port, said inflated balloon causing dilation of the cervical canal, said shaft being removed from the patient when the cervical canal is dilated.

In accordance with a preferred embodiment of the present invention there is provided a cervical canal dilation device which has a shaft for insertion into a cervical canal and inflatable balloons. The cervical canal needs to be dilated for certain procedures that are to be done on the uterus. The shaft has a camera positioned at the tip of the shaft so that the insertion can be viewed by the medical team performing the procedure, enabling the insertion to be safely navigated with minimum pain or discomfort to the patient.

The device is connected to a power supply and a screen displaying the view of the camera.

The shaft has a plurality of ejection orifices formed on its circumference adjacent to the camera so that irrigation fluid can be injected through the shaft and out of the orifices for the purpose of washing off cervical secretions that cloud the camera's view. The orifices may be formed anywhere along the shaft for lubrication substances to be ejected into the cervical canal.

In accordance with another preferred embodiment of the present invention there are provided three inflatable balloons formed on the shaft. One balloon is formed on the tip of the shaft, below the camera, for anchoring the device to the cervical canal. Second and third balloons are formed upstream to the anchoring balloon, for the purpose of dilating the cervical canal.

In accordance with yet another preferred embodiment of the present invention there are provided two inflatable dilating balloons formed on the shaft.

In accordance with an additional preferred embodiment of the present invention there is provided one inflatable dilating balloon formed on the shaft.

In accordance with another preferred embodiment of the present invention there are provided tubes extending internally along the shaft and connected to the balloons for inflation thereof. Each tube has a connection port on the proximal end of the shaft which controls the injection and extraction of inflatable liquids or pressurized gas which inflate the balloons.

Each of the balloons is inflated by injection of saline or any other suitable substance through their corresponding tubes.

The Uterus is viewed by the camera also prior to the inflation of the balloons so that in certain circumstances it can be decided that there is no need for dilating the cervical canal and the shaft may be extracted.

Other features and advantages of the invention will become apparent from the following drawings and description.

BRIEF DESCRIPTION OF THE DRAWINGS

For a better understanding of the invention with regard to the embodiments thereof, reference is made to the accompanying drawings, in which like numerals designate corresponding sections or elements throughout, and in which.

DETAILED DESCRIPTION OF THE EMBODIMENTS

Figure 1:
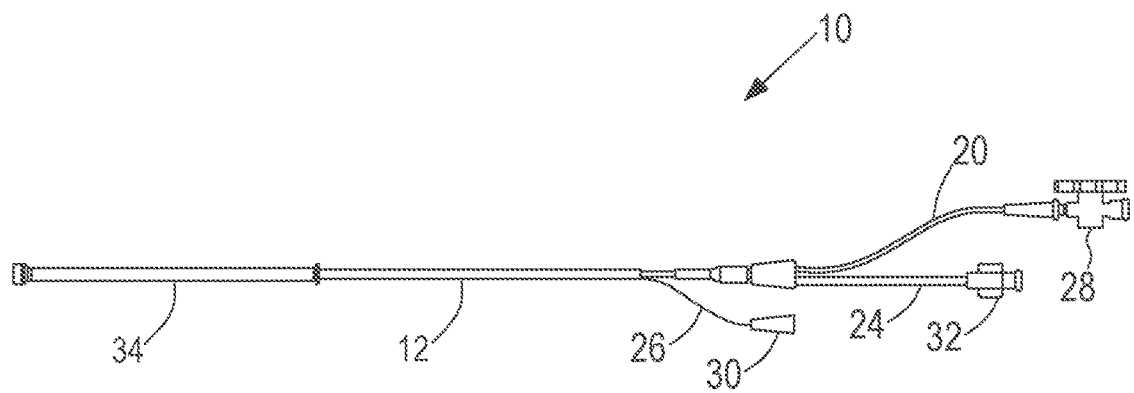
FIG. 1 illustrates an embodiment of a cervical canal dilation device of the present invention, shown with the end portion of its distal side covered by a protection sleeve.

Referring now to FIG. 1 there is shown cervical canal dilation device 10 according to a preferred embodiment of the present invention, which has a hollow shaft 12 having proximal and distal ends. Prior to insertion into the cervical canal, the distal end of shaft 12 is covered by a slidable protective sleeve 34 which protect the balloons 22, 16 and 14 (shown in FIG. 2).

Figure 2:
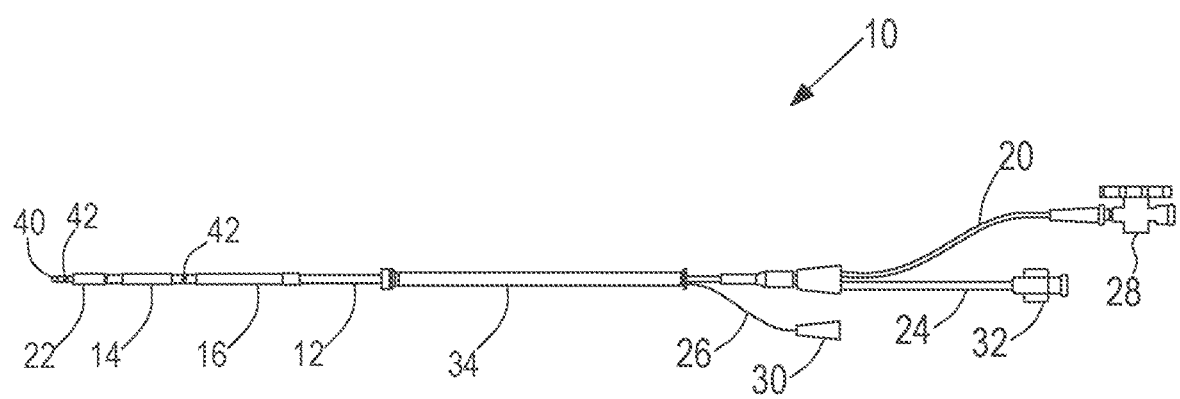
FIG. 2 illustrates the cervical canal dilation device of FIG. 1, with the camera and dilating balloons exposed after the sliding of the protection sleeve.

Referring now to FIG. 2 there is shown hollow shaft 12 with protective sleeve 34 slid to proximal side of shaft 12 to reveal balloons 22, 16, 14 in a deflated configuration, on the distal end. Dilating balloons 14 and 16 are connected to tube 20 which is connected to port 28. Frontal anchoring balloon 22 is connected to tube 26 which is connected to port 30. Tube 24 is connected at one end to port 32 on the proximal end of shaft 12, and on the distal end tube 26 connects to orifices 42. Connection port 32 connects to a syringe (not shown) for injecting cervix dilating fluid which pours out of orifices 42. Orifice 42 represents a plurality of orifices that may be formed anywhere on shaft 12. A camera 40 is positioned on the distal tip of shaft 12 for visualizing the cervical canal 36 (not shown here) during an examination procedure. Camera 40 is wired and provides its images as described further herein (see FIG. 13). Orifice 42 is formed on shaft 12 closely adjacent to camera 40 so that irrigation fluid may be poured out of orifice 42 and wash camera 40 from the secretions secreted by cervical canal 36 and uterus 37 (not shown here). Orifice 42 can also be formed anywhere else on shaft 12, such as the area between balloons 14 and 16 (as shown here).

Figure 3A:
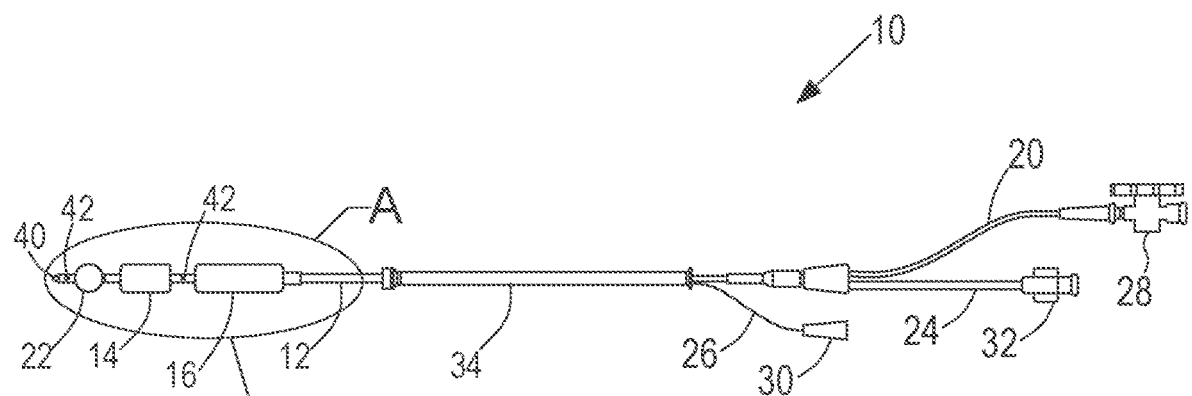
FIG. 3A illustrates the cervical canal dilation device of FIG. 2, showing the anchoring and dilating balloons inflated.
Figure 3B:
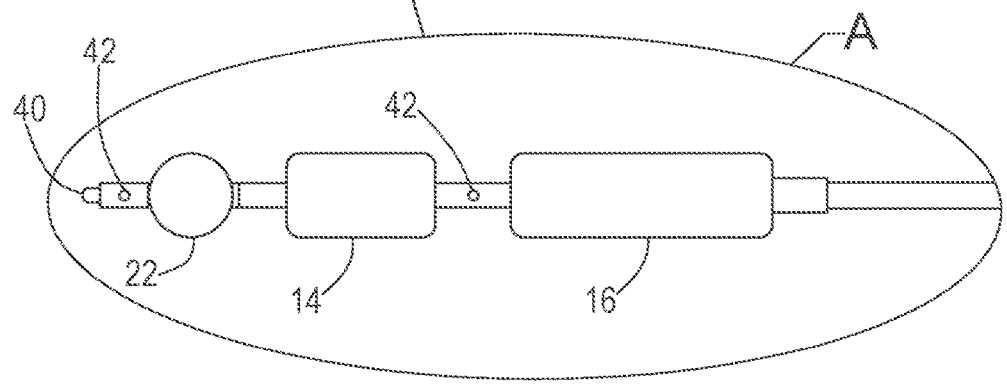
FIG. 3B illustrates a blown-up section of the cervical canal dilation device shown in FIG. 3, showing in detail the camera and the inflated anchoring and dilating balloons.

Referring now to FIGS. 3A-B there is shown cervical canal dilation device 10 illustrating camera 40 situated on the tip of distal end of shaft 12. Camera 40 visualizes the journey of shaft 12 from its entrance to the cervical canal 36 (not shown here) till its destination at the uterus 37 (not shown here) of a patient. Camera 40 projects to screen 44 (shown in FIG. 13) so that the medical team performing the procedure can easily navigate through the cervical canal without injuring and causing pain to the patient.

Formed on distal end of shaft 12, closely adjacent to camera 40, is ejection orifice 42. Irrigation fluid is continually injected out of ejection orifice 42 and onto camera 40 for washing off cervical secretions that cloud camera's 40 view.

FIG. 3B is an enlargement of portion A marked in FIG. 3A.

Figure 4:
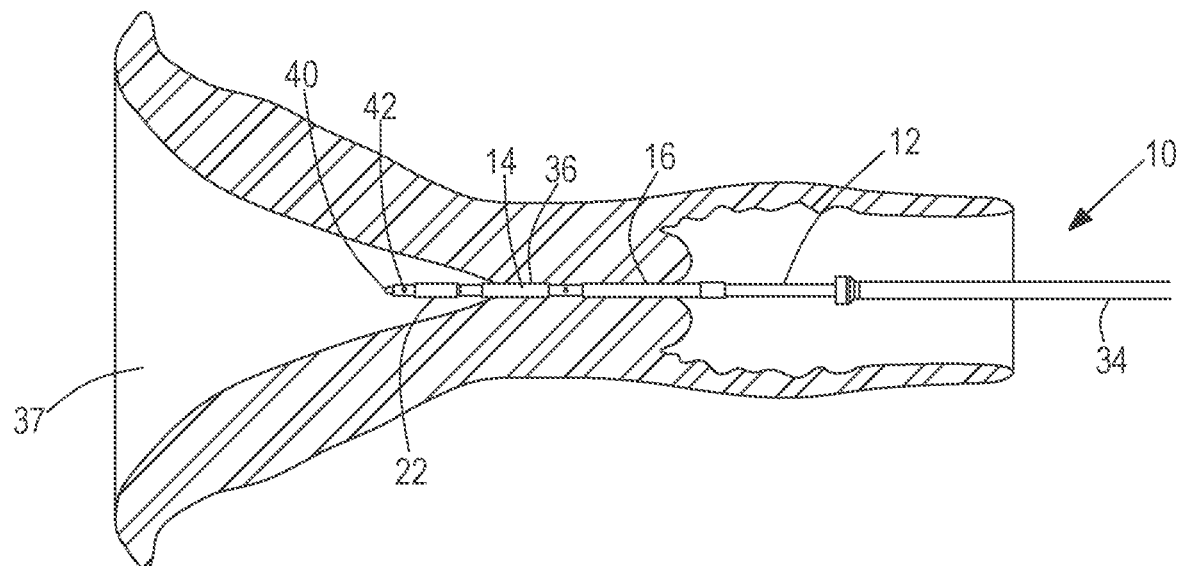
FIG. 4 shows the cervical canal dilation device of FIG. 2 inserted into a cervical canal.

Referring now to FIG. 4 there is shown a partial crosscut view of the reproductive organs of a human female, showing the upper inner-body section of the vagina, the cervical canal 36 and the region of entrance from the cervical canal 36 to the uterus 37. Cervical canal dilation device 10 is inserted in cervical canal 36, in its deflated configuration.

Figure 5:
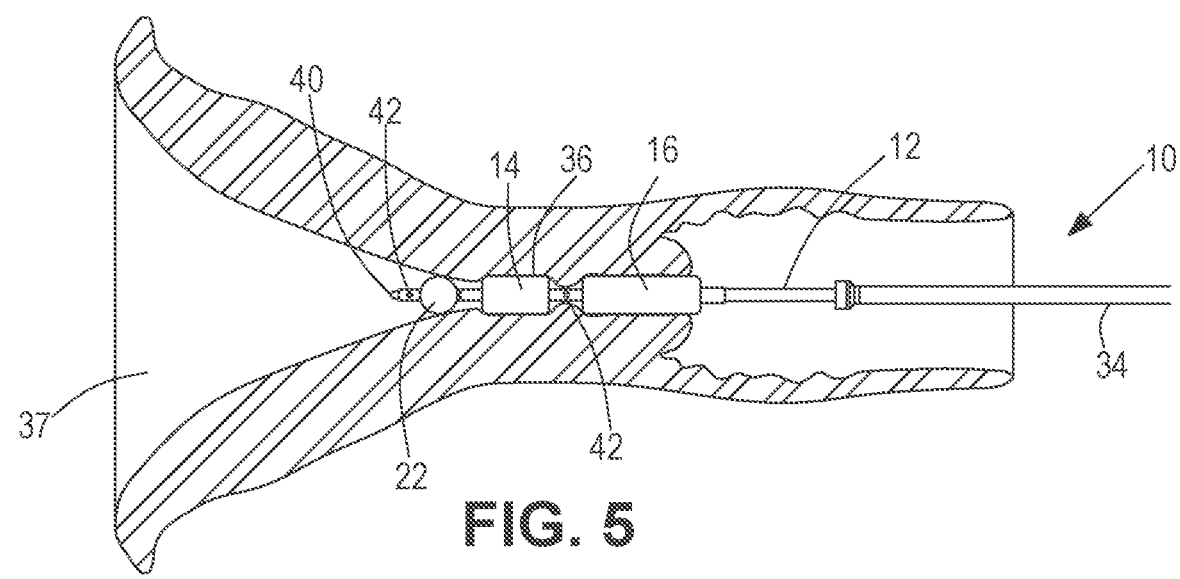
FIG. 5 shows the cervical canal dilation device having the three balloons inflated in the cervix.

Referring now to FIG. 5 there is shown cervical canal dilation device 10 illustrating the three inflatable balloons 22, 14 and 16 in an inflated configuration. Each of balloons 22, 14 and 16 is inflated by injection of saline or any other suitable substance through their corresponding tubes 26 and 20. Connection ports 30, and 28 individually control the injection of the inflatable liquids or pressurized gas and the extraction thereof when deflating balloons 22, 14 and 16. Frontal anchoring balloon 22 is inflated first in order to anchor shaft 12 in the cervix orifice. Once shaft 12 is anchored in place, balloons 14 and 16 are gradually inflated up to approximately 6 atmospheres so that they press against the cervical canal 36, forcing it to dilate.

Uterus 37 is viewed by camera 40 also prior to inflation of balloons 22, 14, 16, so that in certain circumstances it can be decided that there is no need for dilating cervical canal 36 and shaft 12 may be extracted.

Figure 6:
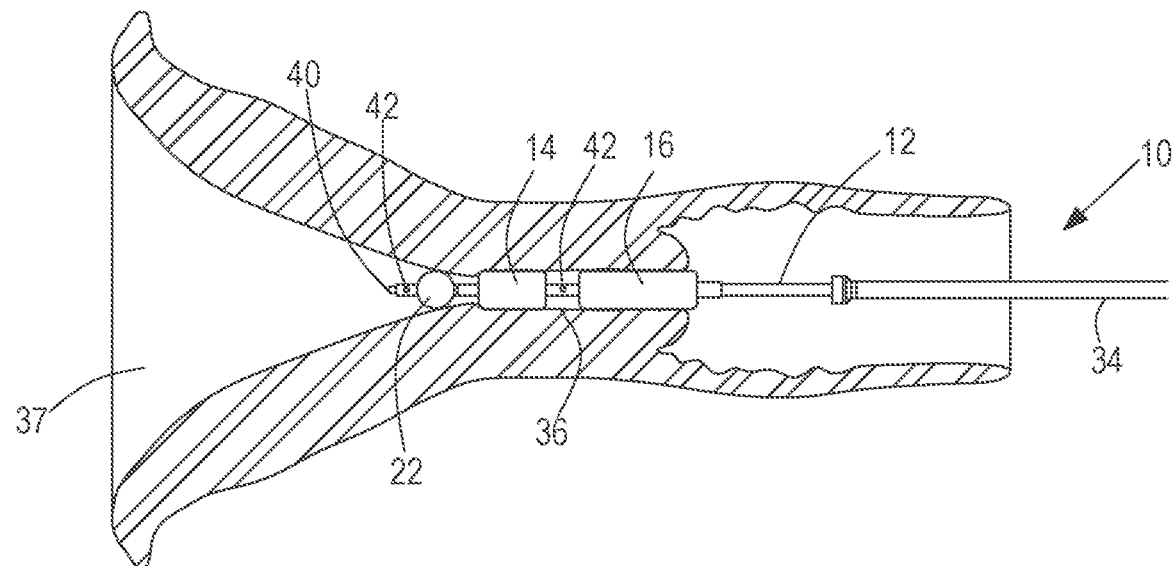
FIG. 6 shows the cervical canal dilated by the cervical canal dilation device of FIG. 5.

Referring now to FIG. 6 there is shown cervical canal 36 dilated after inflation of balloons 14, 16 as shown in FIG. 5. Camera 40 is inside uterus 37 so that uterus 37 may be explored and searched for any findings which are viewed on screen 44.

Figure 7:
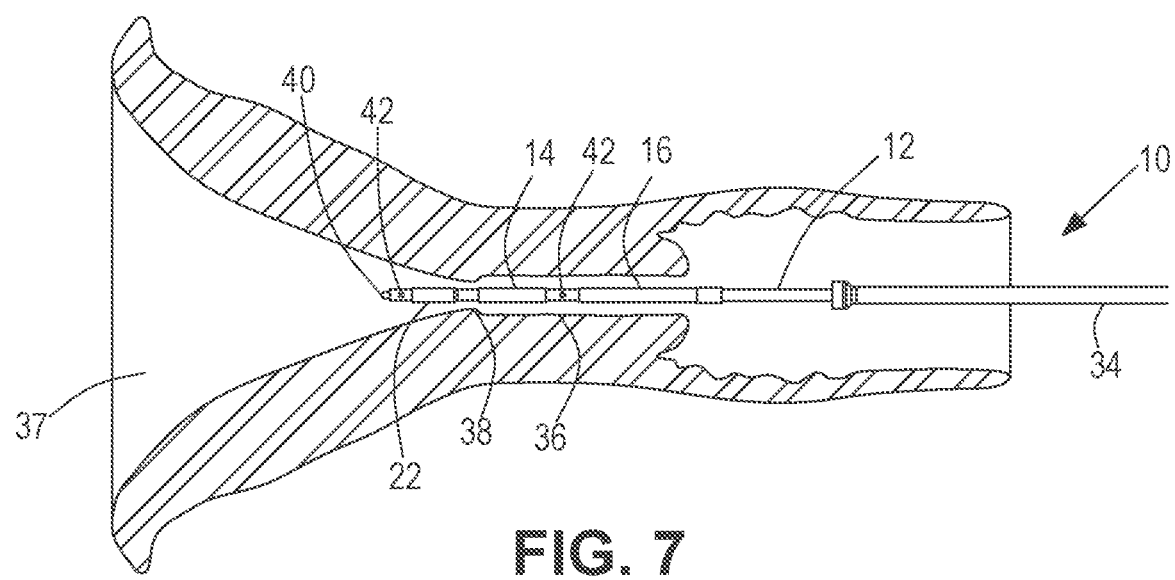
FIG. 7 illustrates the cervical canal dilation device with the dilating balloons and a frontal-anchoring-balloon deflated and the cervix dilated.

Referring now to FIG. 7 there are shown balloons 22, 14, 16 deflated within the dilated cervical canal 36, prior to extraction of shaft 12. Dilating balloons 14 and 16 are gradually deflated through tube 20 and port 28. With dilating balloons 14,16 deflated, the entrapped liquid freely flows out of cervical canal 36 through the outer-body orifice of the canal. Following the deflation of balloons 14 and 16 frontal-restriction-balloon 22 is deflated through tube 26 and port 30. After the three balloons 22, 14, 16 are deflated, cervical canal 36 remains open at both its orifices and they remain with a desired increased width for a considerable time period. The increased width allows the performance of medical treatment procedures to be carried out through the expanded canal.

Figure 8:
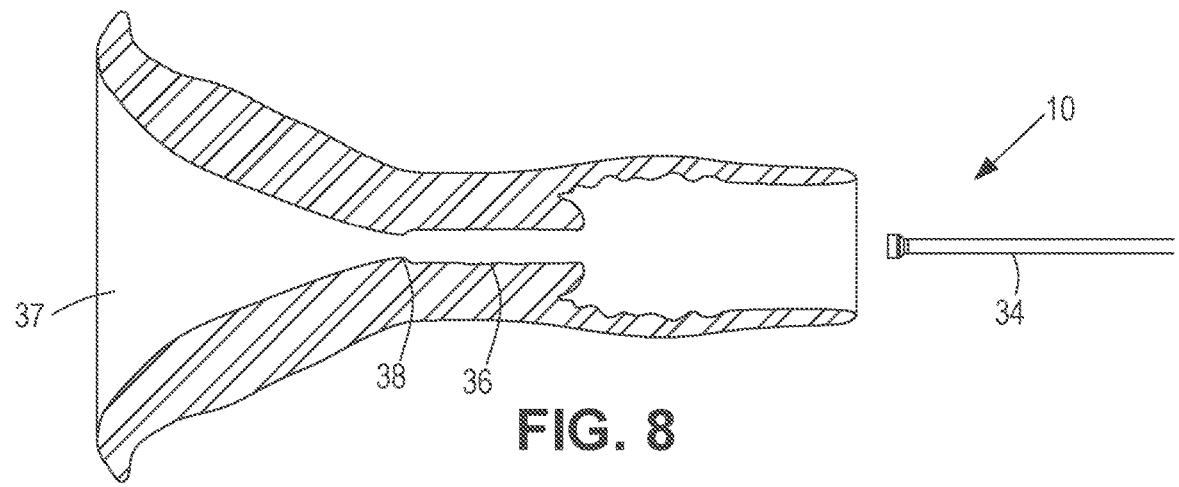
FIG. 8 illustrates the cervical canal dilation device being retracted from the dilated cervix of the patient.

Referring now to FIG. 8 there is shown shaft 12 being extracted from dilated cervical canal 36. Before the removal of shaft 12, slidable protective sleeve 34 is slid towards the distal end of shaft 12 to cover balloons 22, 14, 16. This is done to ensure the smoothness of the surface of shaft 12, thus minimizing the scratching of the wall of the cervical canal 36 upon withdrawing shaft 12.

The inflation of balloons 14, 16 in cervical canal 36 seals the inner and outer body entrances of the cervical canal 36 while increasing the width of the cervical canal 36 in accordance with the extent of the inflation of the balloons, as illustrated in the figure. There are optional graduated markings (not shown) along shaft 12 for facilitating better sealing control of the cervical canal of the treated patient by enabling the exact monitoring of the distances of insertion and withdrawal of cervical canal dilator device into the body of the patient. The graduated markings can be seen through the transparent wall of inflated balloon 16.

Figure 9:
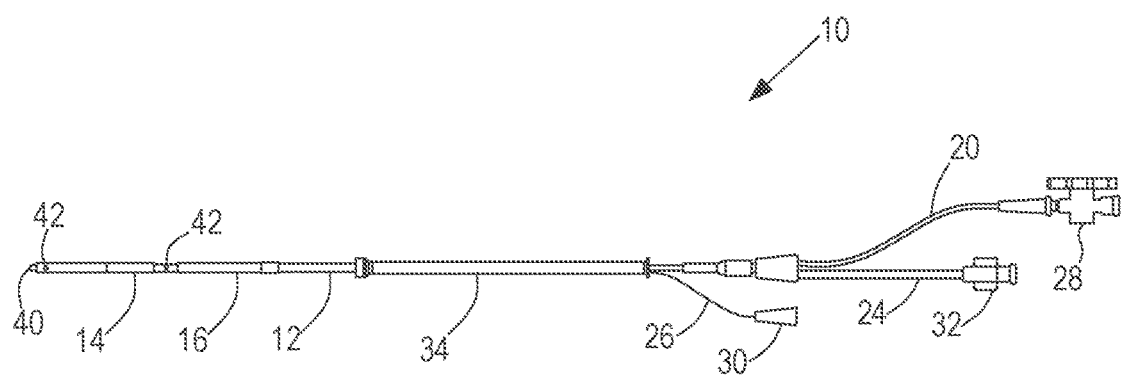
FIG. 9 shows another preferred embodiment of the cervical canal dilation device having only two dilating balloons in a deflated configuration, and a camera.

Referring now to FIG. 9 there is shown another preferred embodiment of the cervical canal dilation device 10 having only two dilating balloons 14, 16, without a frontal anchoring balloon 22. Camera 40 on the tip of distal end of shaft 12 enables display of the insertion of shaft 12 and the entire examination procedure so that the medical staff has a view of cervical canal 36 and uterus 37 so that there is no need for an anchoring balloon.

Figure 10A:
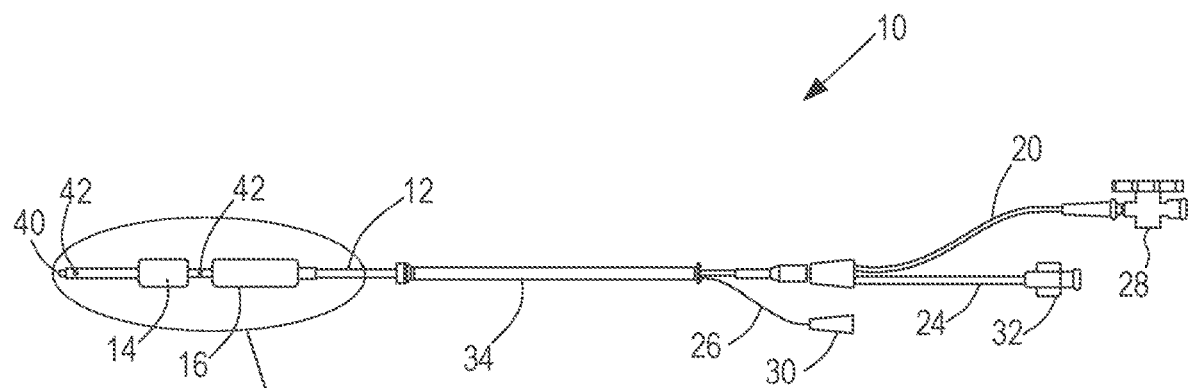
FIG. 10A shows the device of FIG. 9 with the two dilating balloons inflated.
Figure 10B:
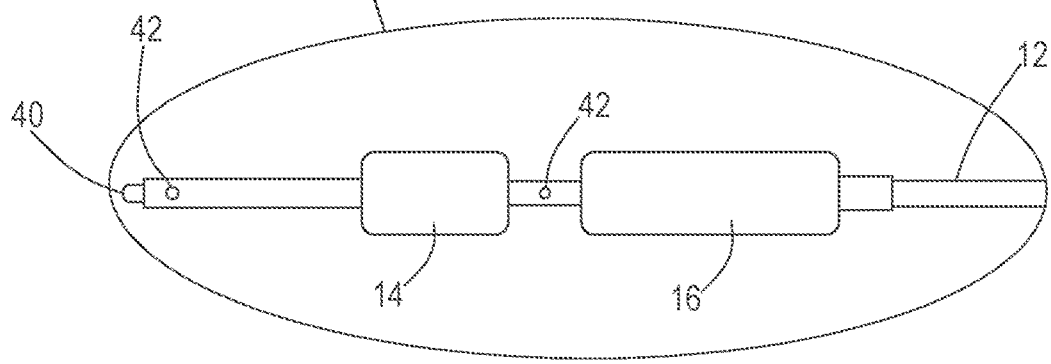
FIG. 10B shows a blown-up section of the cervical canal dilation device shown in FIG. 10A.

Referring now to FIGS. 10A-B there is shown shaft 12 having balloons 14, 16 in an inflated configuration. FIG. 10B is an enlargement of the distal end of shaft 12.

Figure 11:
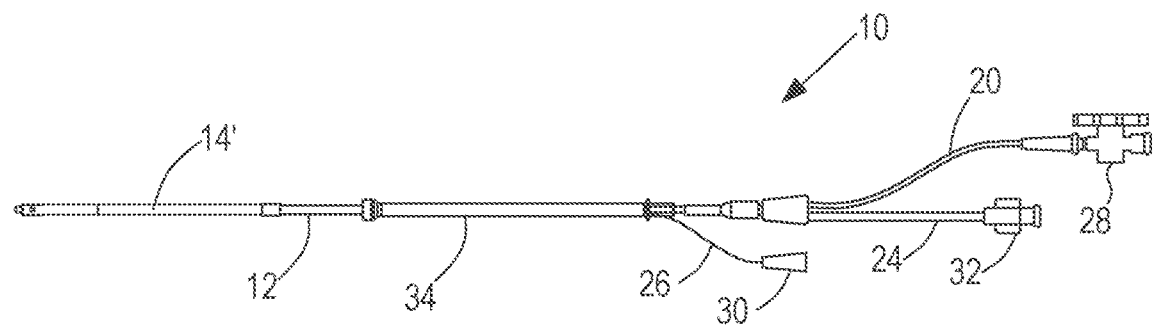
FIG. 11 shows an additional preferred embodiment of the cervical canal dilation device having only one dilating balloon in a deflated configuration.

Referring now to FIG. 11 there is shown yet another preferred embodiment of the present invention, illustrating shaft 12 having only a single inflatable balloon 14 in a deflated configuration. Single inflatable balloon '14 is longer than balloon 14 (as seen in previous Figs.).

Figure 12A:
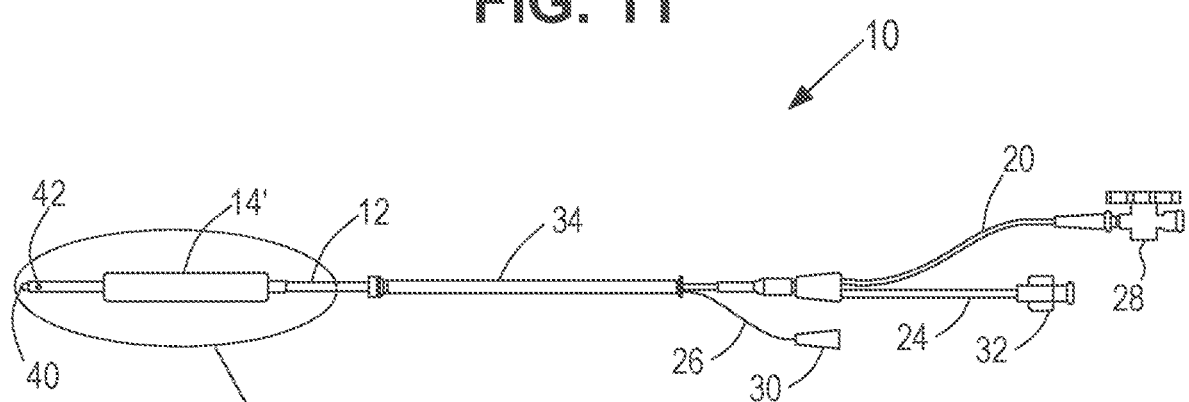
FIG. 12A shows the device of FIG. 11 with the dilating balloon inflated.
Figure 12B:
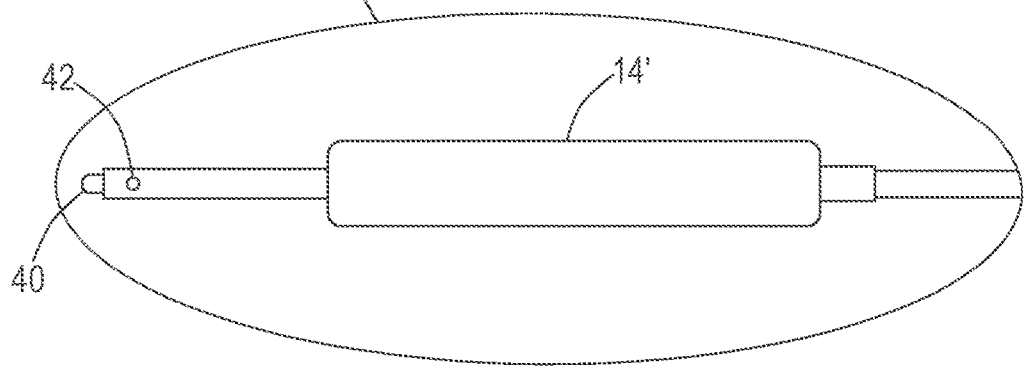
FIG. 12B shows a blown-up section of the cervical canal dilation device shown in FIG. 12A.

Referring now to FIGS. 12A-B, there is shown shaft 12 having single balloon 14' in an inflated configuration.

Referring now to FIG. 12B there is shown an enlargement of distal end of shaft 12 of FIG. 12A, illustrating balloon 14, camera 40 and orifice 42.

Figure 13:
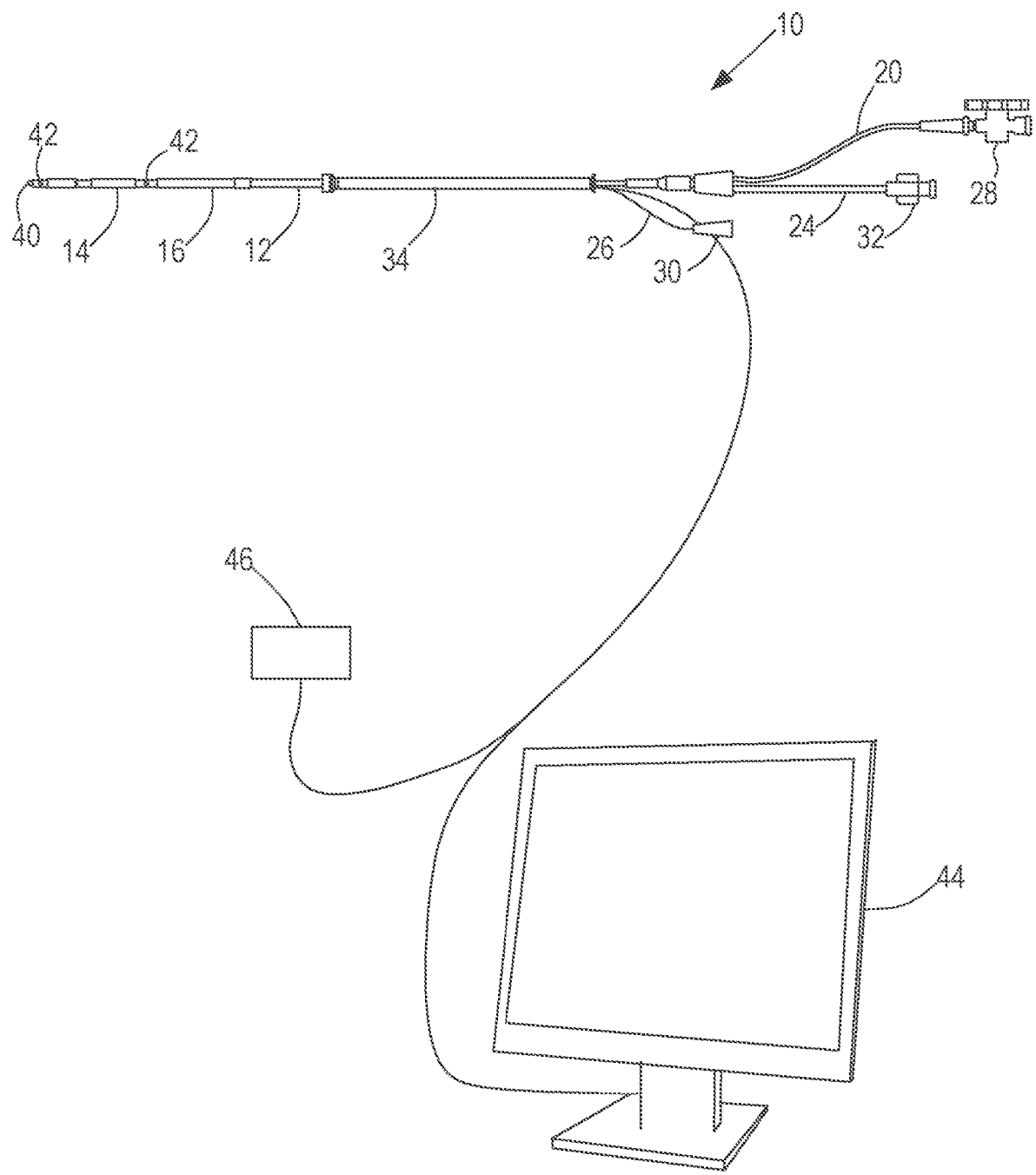
FIG. 13 shows the device of FIG. 2 connected to a power source and a screen.

Referring now to FIG. 13 there is shown dilating device 10 connected to power supply 46 which provides the power for the camera 40. Device 10 is also connected to screen 44 which displays the images taken by camera 40 so that the medical team can monitor the entire procedure.

Having described the invention with regard to particular embodiments thereof, it is to be understood that the description is not meant as a limitation, since further modifications will now become apparent to those skilled in the art, and it is intended to cover such modifications as fall within the scope of the appended claims.

The invention claimed is:

1. A cervical canal dilator device comprising:
   a hollow shaft having a proximal end configured to be positioned upstream and a distal end configured to be positioned downstream, said shaft covered on an end portion of said distal end by a slidable protective sleeve;
   at least one inflatable dilating balloon formed on said distal end of said shaft;
   at least one tube extending internally along said shaft and connected to said at least one inflatable dilating balloon for inflation thereof, each tube of the at least one tube having a connection port on said proximal end of said shaft;
   at least one ejection orifice formed on said shaft including a first ejection orifice formed on a substantially cylindrical wall of said shaft at a first portion of said shaft and including a second ejection orifice formed on the substantially cylindrical wall of said shaft at a second portion of said shaft; and
   a camera situated at the tip of said distal end of said shaft, a light source situated at said distal end of said shaft, for the purpose of illuminating the cervical canal, wherein said shaft is configured to be inserted into a patient's cervical canal while viewing the canal via said camera for guidance, and safe and easy placement of said hollow shaft during said insertion, and wherein said at least one inflatable dilating balloon is inflated by introducing a substance via the connection port or ports of the tube or tubes connected to said at least one inflatable dilating balloon, said at least one inflatable dilating balloon configured upon inflation to cause dilation of the cervical canal, said shaft configured to be removed from the patient when the cervical canal is dilated, wherein the at least one inflatable dilating balloon comprises a first inflatable dilating balloon and a second inflatable dilating balloon and wherein the second ejection orifice is situated on the substantially cylindrical wall of the shaft between the first and the second inflatable dilating balloons, wherein the first ejection orifice is configured so that irrigation fluid is continually injected out of said first ejection orifice and onto said camera for the purpose of washing off cervical secretions that cloud said camera's view and wherein the second ejection orifice is configured for ejection of pressurized dilating liquid into the cervical canal such that a predetermined volume of the pressurized dilating liquid is configured to be injected through the second ejection orifice and into the cervical canal so as to expand the volume of liquid in the cervical canal and thereby dilate the cervical canal, wherein the first ejection orifice is formed on the substantially cylindrical wall of
said shaft at a first location upstream and adjacently to the camera and offset from the camera in a direction along such shaft and wherein the second ejection orifice is formed on the substantially cylindrical wall of said shaft at a second location that is upstream from the camera, is offset from the camera in a direction along such shaft.

2. The device of claim 1, wherein said device is connected to a power supply.

3. The device of claim 1, wherein said device is connected to a screen displaying the view of said camera.

4. The device of claim 1, further comprising an anchoring balloon for anchoring said hollow shaft to the orifice of the uterus.

5. The device of claim 1, further comprising a power supply that is one of a battery and an AC outlet.

6. An orifice and lumen dilator device comprising:
a hollow shaft having a proximal end configured to be positioned upstream and a distal ends configured to be positioned downstream, said shaft covered on an end portion of said distal end by a slidable protective sleeve;
at least one inflatable dilating balloon formed on said distal end of said shaft;
at least one tube extending internally along said shaft and connected to said at least one inflatable dilating balloon for inflation thereof, each tube of the at least one tube having a connection port on said proximal end of said shaft;
at least one ejection orifice formed on said shaft including a first ejection orifice formed on a substantially cylindrical wall of said shaft at a first portion of said shaft and including a second ejection orifice formed on the substantially cylindrical wall of said shaft at a second portion of said shaft; and
a camera situated at the tip of said distal end of said shaft,
wherein said shaft is configured to be inserted into a patient's orifice along the lumen of an organ while viewing the lumen via said camera for guidance, and safe and easy placement of said hollow shaft during said insertion, and wherein said at least one balloon is inflated by introducing a substance via said at least one connection port, said at least one inflatable balloon configured to cause dilation of the orifice and lumen, said shaft configured to be removed from the patient when the lumen is dilated, wherein the first ejection orifice is formed below said camera adjacently thereto, and configured so that irrigation fluid is continually injected through said tube and out of said ejection orifice and onto said camera for the purpose of washing off cervical secretions that cloud said camera's view and wherein the second ejection orifice is configured for ejection of pressurized dilating liquid into a cervical canal such that a predetermined volume of the pressurized dilating liquid is configured to be injected through the second ejection orifice and into the cervical canal so as to expand the volume of liquid in the cervical canal and thereby dilate the cervical canal, wherein the first ejection orifice is formed on the substantially cylindrical wall of said shaft at a first location upstream and adjacently to the camera and offset from the camera in a direction along such shaft.

7. The device of claim 6, wherein said device is connected to a power supply.

8. The device of claim 6, wherein said device is connected to a screen displaying the view of said camera.

9. The device of claim 6, further comprising an anchoring balloon for anchoring said hollow shaft to the orifice of the uterus.

10. The device of claim 6, further comprising a power supply that is one of a battery and an AC outlet.

* * * * *